(12) United States Patent
Nam

(10) Patent No.: US 8,394,433 B2
(45) Date of Patent: Mar. 12, 2013

(54) HAIR GROWTH STIMULANT AND PREPARATION METHOD THEREOF

(76) Inventor: Jong Hyun Nam, Seoul (KR)

( * ) Notice: Subject to any disclaimer, the term of this patent is extended or adjusted under 35 U.S.C. 154(b) by 447 days.

(21) Appl. No.: 12/376,278

(22) PCT Filed: Jul. 26, 2007

(86) PCT No.: PCT/KR2007/003581
§ 371 (c)(1),
(2), (4) Date: Feb. 23, 2009

(87) PCT Pub. No.: WO2008/016230
PCT Pub. Date: Feb. 7, 2008

(65) Prior Publication Data
US 2010/0015256 A1    Jan. 21, 2010

(30) Foreign Application Priority Data
Aug. 3, 2006  (KR) .................. 10-2006-0073498

(51) Int. Cl.
*A61K 36/899* (2006.01)
*A61K 36/906* (2006.01)
*A61K 36/00* (2006.01)

(52) U.S. Cl. ......... 424/769; 424/750; 424/756; 424/725

(58) Field of Classification Search .................. None
See application file for complete search history.

(56) References Cited

FOREIGN PATENT DOCUMENTS

| CA | 2075592 | * | 2/1994 |
|---|---|---|---|
| EP | 07793245.7 | | 9/2011 |
| JP | 63091315 | | 4/1988 |
| JP | 3-209310 | | 9/1991 |
| JP | 3209310 | | 9/1991 |
| JP | 06-135822 | | 5/1994 |
| JP | 6-135822 | | 5/1994 |
| JP | 08-217641 | | 8/1996 |
| JP | 2000-319135 | | 11/2000 |
| JP | 2002-241235 | | 8/2002 |
| JP | 2003-104848 | | 4/2003 |
| KR | 1020060068495 A | | 6/2006 |

* cited by examiner

*Primary Examiner* — Chris R Tate
*Assistant Examiner* — Russell Fiebig
(74) *Attorney, Agent, or Firm* — Workman Nydegger

(57) ABSTRACT

A hair growth stimulant is provided. The hair growth stimulant uses carbonized chestnut burrs that exhibit excellent stimulatory effects on hair restoration and hair growth effects without causing side effect and toxicity. The hair growth stimulant exhibits excellent stimulatory effects on hair restoration without causing any side effect and toxicity in humans and stimulates hair roots to greatly contribute to hair growth. Therefore, the hair growth stimulant is effective in preventing hair loss and grayness. In addition, the hair growth stimulant is formulated into a cream or ointment preparation, which is highly effective in promoting the restoration of hair, to considerably shorten the time required for the treatment of hair loss. Furthermore, the hair growth stimulant uses vegetable ingredients only, thus causing no side effect in humans. Moreover, the hair growth stimulant is softly applicable to the scalp, thus offering convenience in use.

14 Claims, No Drawings

HAIR GROWTH STIMULANT AND PREPARATION METHOD THEREOF

CROSS-REFERENCE TO RELATED APPLICATIONS (not applicable)

STATEMENT REGARDING FEDERALLY SPONSORED RESEARCH OR DEVELOPMENT (not applicable)

THE NAMES OF THE PARTIES TO A JOINT RESEARCH AGREEMENT (not applicable)

INCORPORATION BY REFERENCE OF MATERIAL SUBMITTED ON A COMPACT DISC (not applicable)

BACKGROUND OF THE INVENTION

1. Technical Field

The present invention relates to a hair growth stimulant and a method for preparing the hair growth stimulant. More specifically, the present invention relates to a hair growth stimulant that uses a carbonized form of natural nuts, particularly, carbonized chestnut burrs to achieve excellent stimulatory effects on hair restoration and hair growth effects without any side effects and toxicity, and a method for preparing the hair growth stimulant.

2. Background Art

It has hitherto been known that hair loss is induced by various causes, for example, reduced functions of hair due to male hormones, reduced metabolic activity of hair roots, reduced physiological activity of the scalp, local disorders of blood circulation due to the abnormal conditions of the scalp impeding hair growth, which result from a decrease in the amount of blood flowing through the peripheral blood vessels of the subcutaneous tissues of the head, nutritional deficiencies, stress, side effects of drugs, and hereditary factors. Particularly, hair loss is even more common in people with the gene associated with hair loss. All people with the hair loss-associated gene do not suffer from hair loss. Hair loss does not occur until the hair loss-associated gene is expressed. Age, stress, environmental factors and the like are more closely involved in hair loss.

In general, hair and skin play a significant role in reflecting the functions of the internal organs and the conditions of the body. Hair is a determinant for the beauty, impression and image of individuals. In recent years, stress, insufficient nutrition and excessive ingestion of fast foods have caused damage to the health of hair.

Generally, hairs grow in an area of 700-800 square centimeters ($cm^2$) on the scalp. Thin-haired people have a hair density of 120-130 hairs per square centimeter ($cm^2$), whereas thick-haired people have a hair density of 200-250 hairs per square centimeter ($cm^2$). Normal humans have a total of 70,000-150,000 hairs. Hairs grow about 0.3-0.4 mm every day with the help of nutrients from the blood, but often turn grey or are lost due to the aforementioned environmental factors. Each hair undergoes anagen, catagen and telogen phases, and is finally shed. The period of the anagen phase lasts for 4-5 years in males and 5-6 years in females. Many types of alopecia are known, such as genetic alopecia, seborrheic alopecia, alopecia greata, alopecia due to nutritional deficiencies, alopecia due to the side effects of drugs, alopecia induced by fungi, alopecia due to maladjustment to the environmental change, and psychogenic alopecia. In most of these types of alopecia, the scalp is hot and inflammatory lesions arise at the initial stage of hair loss, and thereafter, hairs gradually become thinner while losing their elasticity.

Although hair loss is induced by the above-mentioned causes, little research has been conducted on the exact causes of hair loss. One reason for this is because hair is barely soluble. This insolubility of hair is an obstacle to the research. Another reason is because the constituent components of hair vary depending on the natural conditions (e.g., race and residential region), diet, etc. Dermatologists around the world reported that mental stress is a main cause of hair loss and ingestion of mineral-rich nutrients is the most ideal therapy for hair loss.

Currently commercially available hair growth stimulants and hair growers include vasodilators, e.g., capronium chloride, minoxidil (Rogaine) and various extracts, hormonal drugs, e.g., estrogen and estradiol, for suppressing the activity of male hormones, and male hormone inhibitors, e.g., pentadecanoic acid and finasteride. The hormonal drugs for suppressing the activity of male hormones and the male hormone inhibitors are clinically ineffective and cause adverse effects, such as inhibition of male functions. Various kinds of drugs, such as Propecia, Tricomin, Spironolactone, cyproterone acetate, Nizoral, Cimetidine and oral contraceptive pills, have been introduced into the market, but their effects have proved to be unsatisfactory. Further, hair growth stimulant compositions containing various extracts suffer from the problem of skin trouble upon application on the skin. In recent years, drugs for treating and preventing alopecia have been developed. For example, FDA-approved minoxidil preparations and Proscar (finasteride) for oral administration, which is a drug inhibiting the activity of 5-alpha-reductase and the subsequent production of dihydrotestosterone, are currently sold as hair growth stimulants. However, these hair growth stimulants are very expensive and are ineffective when being directly applied to the scalp. The drugs are limited in their use because of unexpected side effects upon oral administration.

Thus, there is a continuous need to develop a hair growth stimulant that effectively prevents hair loss and offers convenience in use without any adverse effects, such as skin trouble and inhibition of male functions.

Under these circumstances, the present inventors have conducted intensive studies to develop a hair growth stimulant that completely removes impurities and fats, which are main causes of hair loss, present within hair follicles and promptly regenerates hair follicle cells to achieve maximized hair restoration and growth effects.

As a result, the present inventors have succeeded in developing a hair growth stimulant that uses natural substances non-toxic to humans without the use of any hormone causing a risk of side effects, exhibits a favorable feeling of use and has surprising effects, thus accomplishing the present invention.

BRIEF SUMMARY OF EXAMPLE EMBODIMENTS OF THE INVENTION

Disclosure of Invention

Technical Problem

It is one object of the present invention to provide a hair growth stimulant that uses a mixture of a carbonized form of natural nuts and a vegetable oil as an active ingredient to achieve excellent hair restoration and growth effects without any side effects and toxicity in humans.

It is another object of the present invention to provide a method for preparing the hair growth stimulant.

Technical Solution

In accordance with one aspect of the present invention for achieving the above objects, there is provided a hair growth stimulant including a mixture of carbonized nuts and a vegetable oil as an active ingredient.

The hair growth stimulant of the present invention may be prepared by mixing carbonized chestnut burrs as the carbonized nuts with the vegetable oil in a weight ratio of 1:1-3.

A carbonized form of another kind of nut may be used instead of the carbonized chestnut burrs. Examples of such nuts include pine nuts, gingko nuts, and wild walnuts.

Any general seed oil may be used as the vegetable oil. Specifically, the vegetable oil may be selected from the group consisting of rice bran oil, sesame oil, olive oil, perilla oil, palm oil, castor oil, bean oil, other seed oils, and mixtures thereof. The vegetable oil may be rice bran oil or a mixture of rice bran oil and the selected vegetable oil (e.g., sesame oil) in a weight ratio of 1:3-5.

The hair growth stimulant may further include a ginger concentrate. The weight ratio between the carbonized chestnut burrs/vegetable oil mixture and the ginger concentrate may be 1:0.1-0.5.

The carbonized chestnut burrs used in the hair growth stimulant of the present invention can be obtained by carefully selecting suitable chestnut burrs, washing the selected chestnut burrs with water, drying the washed chestnut burrs, introducing the dried chestnut burrs into a sealed container, and completely incinerating the dried chestnut burrs at 100-300° C. for 1-8 hours. The chestnut burrs as used herein are intended to include their husks, shells and meat.

The vegetable oil may be obtained by general oil extraction processes.

According to an embodiment of the present invention, the rice bran oil may be obtained by passing rice bran through a carbonization furnace at 75-350° C. to evaporate volatile substances, collecting the volatile substances at a temperature of 100-300° C., cooling the collected substances in a cooling tower at 50-75° C., and purifying the cooled substances. The collected substances contain impurities other than rice bran oil. The purification can be performed by known techniques, such as centrifugation. Experimental results reveal that it is preferred to collect the rice bran oil in the temperature range of 250-280° C. The rice bran oil is collected in a low yield at a low temperature. The rice bran oil can be collected at a high temperature but its quality is not good.

The sesame oil can be obtained by carefully selecting suitable sesame seeds using a screening machine so as to prevent introduction of impurities thereinto, washing and drying the selected sesame seeds, parching the dried sesame seeds in a roaster at a temperature of about 160° C. until moisture is completely evaporated from the sesame seeds and smoke begins to appear, pulverizing the parched sesame seeds using a pulverizer, and pressing the sesame seed powder using a press.

The ginger concentrate can be obtained by finely dividing ginger into pieces, extracting the ginger pieces with an extraction solvent in an amount twenty times greater than that of the ginger at 40-100° C. for 4-16 hours to obtain a ginger extract, and heating the ginger extract at 40-70° C. and 50-60 kgf/cm$^2$ until the final concentration reaches ten to thirteen times the concentration of the ginger extract.

The extraction solvent may be purified water or a 30-60% diluted alcohol.

The hair growth stimulant of the present invention may further include at least one adjuvant selected from blood circulation promoters, local stimulants, hair follicle restorers, and anti-inflammatory/antiseptic agents.

In accordance with another aspect of the present invention, there is provided a method for preparing a hair growth stimulant, the method including the steps of: carefully selecting suitable chestnut burrs, washing the selected chestnut burrs with water, drying the washed chestnut burrs, introducing the dried chestnut burrs into a sealed container, completely incinerating the dried chestnut burrs by heating at 100-300° C. for 1-8 hours to obtain carbonized chestnut burrs; preparing a vegetable oil; and mixing the carbonized chestnut burrs with the vegetable oil.

The method of the present invention may further include the step of finely dividing ginger into pieces, extracting the ginger pieces with an extraction solvent in an amount twenty times greater than that of the ginger at 40-100° C. for 4-16 hours to obtain a ginger extract, and heating the ginger extract at 40-70° C. and 50-60 kgf/cm$^2$ until the final concentration reaches ten to thirteen times the concentration of the ginger extract.

The vegetable oil may be rice bran oil or a mixture of rice bran oil and at least one vegetable oil selected from sesame oil, castor oil and edible oil.

The rice bran oil can be obtained by passing rice bran through a carbonization furnace at 75-350° C. to evaporate volatile substances, collecting the volatile substances, cooling the collected substances in a cooling tower at 50-75° C., and purifying the cooled substances.

DETAILED DESCRIPTION OF EXAMPLE EMBODIMENTS OF THE INVENTION

Best Mode for Carrying Out the Invention

The present invention will now be described in more detail.

The present invention provides a hair growth stimulant including a mixture of carbonized chestnut burrs and a vegetable oil as an active ingredient.

According to an embodiment of the present invention, the hair growth stimulant may be prepared by mixing the carbonized chestnut burrs with the vegetable oil in a weight ratio of 1:1-3. If the vegetable oil is used in an amount smaller than the lower limit (i.e. 1:1), the hair growth stimulant offers an unfavorable feeling, causing inconvenience in use. Meanwhile, if the vegetable oil is used in an amount greater than the upper limit (i.e. 1:3), the hair restoration effects of the hair growth stimulant are negligible.

A carbonized form of another kind of nut may be used instead of the carbonized chestnut burrs. Examples of such nuts include pine nuts, gingko nuts, and wild walnuts.

Any general seed oil may be used as the vegetable oil. Specifically, the vegetable oil may be selected from the group consisting of rice bran oil, sesame oil, olive oil, perilla oil, palm oil, castor oil, bean oil, other seed oils, and mixtures thereof. The vegetable oil may be rice bran oil or a mixture of rice bran oil and the selected vegetable oil in a weight ratio of 1:3-5. Since the rice bran oil has a higher degree of unsaturation than other vegetable oils, it causes no danger of decay and skin trouble (e.g., skin speckles) in skin response. The rice bran oil may be used alone. From the economical viewpoint, a mixture of the rice bran oil and another vegetable oil may be used. A relatively low content of the rice bran oil is not favorable because the intended effects of the rice bran oil are not satisfactory. Meanwhile, a relatively high content of the rice bran oil is economically disadvantageous. The rice bran oil may be obtained by carefully selecting rice bran free from impurities, washing the selected rice bran with water, drying the washed rice bran, passing the dried rice bran through a carbonization furnace at 75-350° C. to evaporate volatile substances, collecting the volatile substances at temperature intervals (for example, 25° C.), cooling the collected substances in a cooling tower at 50-75° C., and purifying the cooled substances. The collected substances may contain impurities other than rice bran oil. The impurities may be removed by general purification techniques, such as centrifugation (7,500 rpm).

Rice bran refers to a pulverized mixture of pericarp, testa, aleurone, etc. generated when brown rice is milled to obtain white rice and is also read as 'Migang' in Chinese. Rice bran makes up 6-8% of brown rice. An increase in the degree of milling of brown rice results in the production of a large amount of rice bran. The ingredients of rice bran vary depending on the degree of milling of brown rice. Specifically, as the degree of milling of brown rice increases, the contents of fats, vitamin B 1 and phosphorus increase and the content of fibers decreases. This reason is because the constituent ingredients of brown rice are present in different amounts from the shell to the core of the brown rice. The standard chemical composition of rice bran is as follows: 13.5% moisture, 13.2% proteins, 18.3% fats, 38.3% carbohydrates, 7.8% fibers, 8.9% ashes, etc. 2.5 mg of vitamin B 1 and a sufficient amount of vitamin E are present in 100 g of rice bran.

For example, sesame oil as the vegetable oil can be obtained by the following procedure. First, suitable sesame seeds are carefully selected using a screening machine so as to prevent introduction of impurities thereinto, washed, and dried. Thereafter, the dried sesame seeds are parched in a roaster at a temperature of about 160° C. until moisture is completely evaporated from the sesame seeds and smoke begins to appear. The parched sesame seeds are pulverized using a pulverizer and pressed using a press to obtain sesame oil. Sesame is an annual plant, 90-150 cm tall, that has short hairs and elongated oval or willow leaf-shaped leaves facing each other. When sesame fruits mature in 8-9 months, stems are cut, tied in a bundle, dried in the sun. The bundle was shaken and impurities are removed to collect sesame seeds only. The black sesame seeds are used as drug materials and the white sesame seeds are used as oil materials. The dried seeds are pressed to obtain a yellow and fragrant oil. The oil is miscible with ether, chloroform and petroleum ether, and is slightly soluble in alcohol. The oil is hardened at 0-5° C. The oil has a specific gravity of about 0.9 and a refractive index of about 1.5. The oil has an acid number not higher than 2, a saponification number of 188-195 and an iodine number of 103-116. The oil is a glyceride of oleic acid, linoleic acid, palmitic acid, stearic acid, arachic acid, lignoceric acid, and other acids.

The hair growth stimulant may further include a ginger concentrate. The weight ratio between the carbonized chestnut burrs/vegetable oil mixture and the ginger concentrate is 1:0.1-0.5. The ginger concentrate is added to sterilize the skin due to its antiseptic activity and to enhance the preservation of the final hair growth stimulant, thus enabling long-term storage of the hair growth stimulant. Accordingly, when the content of the ginger concentrate is less than 1, the antiseptic effects of the hair growth stimulant are deteriorated. Meanwhile, when the content of the ginger concentrate is more than 3, skin irritation may be caused.

The carbonized chestnut burrs used in the hair growth stimulant of the present invention can be obtained by the following procedure. First, suitable chestnut burrs are carefully selected, washed with water, dried, introduced into a sealed container, and completely incinerated at 100-300° C. for 1-8 hours. The chestnut burrs as used herein are intended to include their husks, shells and meat. The use of fruits (i.e. chestnuts) of chestnut trees is preferred. Chestnut husks, shells or meat only may also be used. Since there is no significant difference in use between chestnut husks, shells and meat, the use of chestnut husks and shells is preferred taking into consideration the fact that chestnut meat is an important source of income of farmers.

According to an embodiment of the present invention, a carbonized form of another kind of nut may be used instead of the carbonized chestnut burrs. Examples of such nuts include pine nuts, gingko nuts, and wild walnuts. Nuts are dry indehiscent fruits that do not split open at maturity. A typical nut includes two or more shells, each of which has one or more seeds. Like grains and beans, edible portions of nuts are derived from cotyledon. Examples of such nuts include pine nuts, chestnuts, gingko nuts, wild walnuts, acorns and walnuts. Small-sized nuts are referred to 'nutlets' and can be found in water peppers, leaves of *Perilla frutescens*, etc. Similar nuts found in yew trees, *Viburnum carlesii*, etc. do not composed of ovaries and are thus referred to 'quasi-nuts'. Carbonized forms of the nutlets and quasi-nuts may be used to prepare hair growth stimulants in the same manner as in the preparation of the hair growth stimulant using the carbonized chestnut burrs in accordance with the present invention.

The carbonized chestnut burrs are passed through a sieve (100-300 mesh) to obtain a fine powder of the carbonized chestnut burrs. A sieve of 180-250 mesh is preferably used. As the pore size of the sieve decreases, the powder of the carbonized chestnut burrs becomes finer. The use of a finer powder of the carbonized chestnut burrs is advantageous in terms of hair restoration effects and performance of the hair growth stimulant, but may cause clogging of hair follicles of the scalp. Accordingly, it is preferable to limit the size of the powder to the predetermined range. As the pore size of the sieve increases, the powder of the carbonized chestnut burrs is roughened, thus resulting in an unfavorable feeling of use.

Chestnut burrs constituting the active ingredient of the hair growth stimulant according to the present invention are prickly husks enclosing chestnuts. Chestnut tree is a deciduous woody dicotyledonous plant of the order Fagaceae belonging to the family Fagaceae, and its botanical name is *Castanea crenata* var. dulcis. Chestnut trees are distributed in the temperate regions of Asia, Europe, North America, North Africa, etc. Chestnuts are fruits of chestnut trees and mature on September or October. One to three chestnuts are included in one chestnut bur. Thirteen plants belonging to the genus *Castanea* are distributed in the temperate regions of Asia, Europe, North America, North Africa, etc. Chestnut species whose fruits are of particular importance are *C. crenta, C. sativa, C. mollissima* and *C. dentate*. Chestnut burrs as raw materials of the carbonized chestnut burrs can be collected from chestnut trees. The chestnut burrs include their husks, shells and meat.

The ginger concentrate can be obtained by finely dividing ginger into pieces, extracting the ginger pieces with an extraction solvent in an amount twenty times greater than that of the ginger at 40-100° C. for 4-16 hours to obtain a ginger extract, and heating the ginger extract at 40-70° C. and 50-60 kgf/cm$^2$ until the final concentration reaches ten to thirteen times the concentration of the ginger extract. According to an embodiment of the present invention, the ginger extract has a concentration of about 6%, and thereafter, it may be concentrated to a concentration of about 75%.

Ginger as a raw material of the ginger concentrate is used in cooking foods. Representative pharmacological effects of ginger are: 1) to activate the metabolic functions to induce sweating and appease phlegm, and to control the blood circulation and body temperature to alleviate a fever and recover from a wind-cold; 2) to promote urination to prevent facial swelling and roughness; and 3) to stimulate the secretion of digestive fluids and promote the movement of the stomach and intestines to improve appetite, and to assist digestive absorption due to the presence of proteases and flavoring ingredients. In addition, ginger has recently proved to be more effective than conventional antinauseants. Ginger is effective in stopping indigestion, nausea and hiccups. The scientific name of ginger is *Zingiber officinale* Rosc., and ginger is read as 'Shouga' in Japanese. Ginger is a herbaceous perennial of the class Monocotyledoneae belonging to the family Zingiberaceae, the order Zingiberales. 47 genera and 1,400 species of ginger are found around the world. Ginger is distributed in tropical regions, such as India and the Malay Archipelago. Two ginger species are known to grow in Korea. The genus *Zingiber* grows in the tropical and subtropical regions of Asia. Two ginger species are currently cultivated in Korea, and include a ginger whose rhizome is used as a material for spices and *Zingiber mioga* Rosc. whose buds and spikes are edible.

The hair growth stimulant of the present invention may further include at least one adjuvant selected from blood circulation promoters, local stimulants, hair follicle restorers, and anti-inflammatory/antiseptic agents.

The present invention also provides a method for preparing a hair growth stimulant, the method including the steps of: carefully selecting suitable chestnut burrs, washing the selected chestnut burrs with water, drying the washed chestnut burrs, introducing the dried chestnut burrs into a sealed container, completely incinerating the dried chestnut burrs by heating at 100-300° C. for 1-8 hours to obtain carbonized chestnut burrs; preparing a vegetable oil; and mixing the carbonized chestnut burrs with the vegetable oil.

The carbonized chestnut burrs, the rice bran oil and the ginger concentrate are obtained by the respective procedures described above.

Hair goes through a repeated growth cycle consisting of anagen, catagen and telogen phases. Hair grows in the anagen phase only and stops its growth in the catagen phase, resulting in hair loss. The hair growth stimulant of the present invention lengthens the catagen phase and supplies nutrients to hair in the telogen phase to return the hair to healthy hair at the initial stage of growth, thereby allowing hair to rapidly grow and promoting the growth of hair. That is, the hair growth stimulant of the present invention serves to protect and grow hair in the anagen phase.

The hair growth stimulant of the present invention may be formulated into known ordinary forms. For example, the hair growth stimulant may be formulated into preparations for topical application, such as ointments and creams.

The hair growth stimulant of the present invention may also be presented into various cosmetic formulations for hair and scalp care, such as hair lotions, hair creams, hair gels, hair rinses and essences. Conventional hair lotions, hair creams, hair gels and hair rinses contain no hair growth stimulant and are used for the purpose of beauty only. Accordingly, conventional cosmetic formulations are seldom helpful in promoting the growth and restoration of hair. The hair growth stimulant of the present invention can be added to various hair cosmetic compositions to produce functional hair cosmetics. The hair growth stimulant of the present invention supplies nutrients to hair of people who do not feel lack of hair but lose its elasticity due to environmental factors and stress, and hair of male and female patients with alopecia to render the hair more glossy and healthy.

So long as the effects of the present invention are not sacrificed, if necessary, the hair growth stimulant of the present invention may further include one or more additives that are used typically in cosmetics and medicines. Examples of such additives include plant extracts, oily ingredients, surfactants, alcohols, fatty acids, preservatives, antioxidants, colorants, fragrances, UV absorbers, viscosity modifiers, chelating agents, pH-adjusting agents, vitamins, and tablets.

An ointment or cream preparation using the hair growth stimulant of the present invention can be produced by the following procedure. First, carbonized chestnut burrs, sesame oil and optionally a crude drug extract are mixed together. The mixture is mixed with appropriate amounts of an organic acid, VASELINE® (petroleum jelly) and an excipient. The resulting mixture is formulated by a known formulation technique to produce an ointment or cream preparation. The ointment or cream preparation include 0.1 to 30% by weight, preferably 5 to 20% by weight, of the mixture of the carbonized chestnut burrs, the sesame oil and the crude drug extract as an active ingredient. When the active ingredient is present in an amount of less than 0.1% by weight, the hair growth and restoration effects of the preparation are insignificant. Meanwhile, when the active ingredient is present in an amount of more than 30% by weight, it is difficult to formulate into the preparation and an excessive amount of the active ingredient does not contribute to further improvement of hair growth and restoration effects.

The pH of the hair growth stimulant according to the present invention is preferably in the range of 4 to 7 taking into consideration human safety, absorption of the constituent ingredients into the scalp, prevention of decay of the constituent ingredients, and affinity of the constituent ingredients for the skin.

The present invention will be explained in more detail with reference to the following examples and comparative examples. However, these examples are given for the purpose of illustration only and are in no way intended to limit the scope of the invention.

Mode for the Invention

EXAMPLES

Example 1

Chestnut burrs having a predetermined size were carefully selected from Korean native chestnut trees. The selected chestnut burrs were washed with purified water and dried in the shade. Identification as to whether the chestnut burrs were completely dried or not was made. 1,000 g of the dried chestnut burrs were introduced into a tightly sealed container and completely incinerated in the container at about 300° C. for about 8 hours. The incinerated chestnut burrs were allowed to stand for 2 hours to obtain carbonized chestnut burrs. The carbonized chestnut burrs were passed through a 180-mesh sieve to obtain about 800 g of a powder of the carbonized chestnut burrs.

Rice bran was carefully passed through a screening machine so as to prevent introduction of impurities thereinto, washed, and completely dried. 4,000 g of the dried rice bran was passed through a carbonization furnace at 300° C. to evaporate volatile substances. The volatile substances were collected at 250° C., and left to stand in a cooler at 24° C. for 12 hours to obtain 600 g of rice bran oil.

500 g of the powder of the carbonized chestnut burrs were mixed with 500 g of the rice bran oil with stirring, and then a general excipient was added thereto until the content of the mixture of the powder and the oil reached 80% by weight. The resulting mixture was formulated by a cream formulation technique known in the art to prepare a hair growth stimulant.

Example 2

Suitable ginger was selected. 1,500 g of purified water was added to 500 g of the selected ginger. The mixture was subjected to extraction at about 40° C. for 8 hours, and then the ginger was removed to obtain 1,500 g of a 6% ginger extract. The ginger extract was heated at 70° C. at a pressure of 60 kg/cm² until the final concentration reached 75% and cooled to room temperature to obtain a ginger concentrate.

A hair growth stimulant was prepared in the same manner as in Example 1, except that 50 g of the ginger concentrate was added to 500 g of the mixture of the powder of the carbonized chestnut burrs and the rice bran oil.

Example 3

Suitable sesame seeds were carefully selected using a screening machine so as to prevent introduction of impurities thereinto, washed, dried, parched in a roaster at a temperature of about 160° C. until moisture was completely evaporated from the sesame seeds and smoke began to appear, pulverized using a pulverizer, and pressed using a press to obtain sesame oil.

A hair growth stimulant was prepared in the same manner as in Example 2, except that a mixture of the rice bran oil and the sesame oil (⅓) was used instead of the rice bran oil.

Example 4

A hair growth stimulant was prepared in the same manner as in Example 2, except that 60 g of the rice bran oil, 30 g of the powder of the carbonized chestnut burrs and 9 g of the ginger concentrate were used.

Example 5

A hair growth stimulant was prepared in the same manner as in Example 3, except that 40 g of a mixture of vegetable oils (rice bran oil: sesame oil=1:4), 25 g of the powder of the carbonized chestnut burrs and 7.5 g of the ginger concentrate were used.

Example 6

A hair growth stimulant was prepared in the same manner as in Example 3, except that 50 g of a mixture of vegetable oils (rice bran oil: sesame oil=1:5), 20 g of the powder of the carbonized chestnut burrs and 10 g of the ginger concentrate were used.

Example 7

A hair growth stimulant was prepared in the same manner as in Example 3, except that 60 g of a mixture of vegetable oils (rice bran oil: sesame oil=1:3), 20 g of the powder of the carbonized chestnut burrs and 8 g of the ginger concentrate were used.

Comparative Example 1

A hair growth stimulant was prepared in the same manner as in Example 1, except that 30 g of an oak charcoal powder, 30 g of edible oil and 40 g of sesame oil were used. The hair growth stimulant was used as a placebo.

Comparative Example 2

A minoxidil product available from American Hairloss R&D Institute (AHRDI) was used as a preparation for comparison.

Experimental Example 1

Hair Restoration Stimulation Experiments

One hundred twenty male patients with alopecia were divided into six groups, 20 patients per group. The hair growth stimulants prepared in Examples 1 to 6 were applied to the bald sections of the scalp three times daily in the respective groups. The patients carefully massaged their bald sections for 3-5 minutes to homogeneously apply the respective hair growth stimulants. At this time, the massage was performed using fingertips such that the scalp was not injured. The hair density and thickness of the patients were measured at 15 day intervals over 3 months from the beginning of experiments. The hair density and thickness measurements were implemented using a Folliscope System Using Phototricogram (LeadM). Specifically, the hair density was determined by taking photographs of the bald sections using a magnifying lens (60×), counting the number of hair follicles per unit area (1 cm²) in the photographs, and automatically totaling the counts. The hair thickness was determined by taking photographs of the bald sections using a magnifying lens (200×) and averaging the thickness of three hairs in the photographs. The results are shown in Table 1.

TABLE 1

|  | Hair density (EA/cm²) | Hair thickness (□) | Hair irritation | Final evaluation Effective | Final evaluation Ineffective |
|---|---|---|---|---|---|
| Example 1 | 180 | 85 | Not observed | 17 | 3 |
| Example 2 | 182 | 89 | Not observed | 18 | 2 |
| Example 3 | 188 | 87 | Not observed | 16 | 4 |
| Example 4 | 197 | 95 | Not observed | 19 | 1 |
| Example 5 | 180 | 83 | Not observed | 16 | 4 |
| Example 6 | 174 | 75 | Not observed | 17 | 3 |
| Total |  |  |  | 103 | 17 |

※ Average hair density of Korean - 106 EA/cm²

※ Average hair thickness of Korean - Lanugo (undergoing hair loss) <40□, Vellus hair: 40-60□, Terminal hair: 60-120□

As can be seen from the experimental results of Table 1, the preparation of Example 4 showed better stimulatory effects on hair restoration.

Experimental Example 2

Hair Restoration Stimulation Experiments for Comparison

Eighteen male patients with alopecia were divided into three groups, 6 patients per group. The preparation of Example 4, which was proved to have good stimulatory effects on hair restoration, the placebo and the minoxidil product were spread on the bald sections of the respective scalps twice a day, i.e. in the morning and after hair washing in the evening, in the respective groups. The patients carefully massaged their bald sections for 3-5 minutes to homogeneously apply the respective preparations. At this time, the massage was performed using fingertips such that the scalp was not injured. To obtain consistent data, the patients were allowed to use the same shampoos and eat two boiled eggs daily.

The hair density and thickness of the patients were measured by taking photographs at 10 day intervals over 3 months from the beginning of clinical experiments.

The hair density and thickness measurements were implemented using a Folliscope System Using Phototricogram (LeadM). Specifically, the hair density was determined by taking photographs of the bald sections using a magnifying lens (60×), counting the number of hair follicles per unit area (1 cm$^2$) in the photographs, and automatically totaling the counts. The results are shown in Table 2.

The hair thickness was determined by taking photographs of the bald sections using a magnifying lens (200×) and averaging the thickness of three hairs in the photographs. The results are shown in Table 3.

TABLE 2

(Unit: EA/cm$^2$)

| Time (day) | 0 | 10 | 20 | 30 | 40 | 50 | 60 | 70 | 80 | 90 |
|---|---|---|---|---|---|---|---|---|---|---|
| Hair growth stimulant (Example 4) | 132 | 135 | 140 | 147 | 156 | 167 | 176 | 185 | 189 | 197 |
| Placebo | 135 | 135 | 136 | 135 | 137 | 138 | 138 | 139 | 140 | 143 |
| Minoxidil product | 134 | 135 | 137 | 137 | 138 | 140 | 142 | 142 | 145 | 145 |

※ Average hair density of Korean: 106 EA/cm$^2$

As is apparent from the results of Table 2, after about 20 days following the spreading of the hair growth stimulant (Example 4), the hair density continuously increased. 90 days after the measurement, the hair density reached 197 EA/cm$^2$, which was higher by 65 EA/cm$^2$ than that before the spreading.

As for the placebo, only a slight increase (8 EA/cm$^2$) was observed in hair density before and after the spreading. As for the minoxidil product, a large increase in hair density was observed for one month after the spreading, and thereafter, a slight increase was observed until 90 days. There was only a slight increase (11 EA/cm$^2$) before and after the spreading.

From these observations, it could be concluded that the hair growth stimulant (Example 4) was more effective in promoting the restoration of hair than the placebo and the minoxidil product.

TABLE 3

(Unit: □)

| Time (day) | 0 | 10 | 20 | 30 | 40 | 50 | 60 | 70 | 80 | 90 |
|---|---|---|---|---|---|---|---|---|---|---|
| Hair growth stimulant (Example 4) | 55 | 58 | 60 | 62 | 71 | 80 | 84 | 89 | 93 | 95 |
| Placebo | 48 | 48 | 48 | 48 | 49 | 48 | 47 | 48 | 49 | 50 |
| Minoxidil Product | 50 | 55 | 55 | 58 | 58 | 60 | 60 | 62 | 62 | 64 |

※ Average hair thickness of Korean - Lanugo < 40 □, Vellus hair: 40-60 □, Terminal hair: 60-120 □

As is evident from the results of Table 3, after about 20 days following the spreading of the hair growth stimulant (Example 4), the hair thickness increased. 90 days after the measurement, the hair thickness reached 95□, which was higher by 40□ than that before the spreading.

As for the placebo, only a slight difference (2□) was observed in hair thickness before and after the spreading. As for the minoxidil product, a large increase in hair thickness was observed for one month after the spreading, and thereafter, a slight increase was observed until 90 days. There was only a slight increase (14□) before and after the spreading.

From these observations, it could be concluded that the hair growth stimulant (Example 4) was more effective in promoting the restoration of hair than the placebo and the minoxidil product.

Experimental Example 3

Stability (Scalp Irritation) Experiments

The scalp examination was conducted using a Folliscope System Using Phototricogram (LeadM). Specifically, the scalp states of the patients were judged by taking photographs of the scalps using a magnifying lens (60×) at 10 day intervals over 3 months from the beginning of clinical experiments, and comparing the photographs with the following reference scalp states (total 30 types):

Normal Scalp States (2 Types)
N-I: Scalp with high density and large thickness
N-II: Scalp with relatively high density and relatively large thickness
Dry Scalp States (4 Types)
D-I: Scalp on which horny scales were slightly observed
D-II; Scalp on which horny scales were observed
D-III: Scalp on which horny scales were excessively observed
D-IV: Scalp on which small dandruff pieces were observed
Sensitive Scalp States (2 Types)
S-I: Sensitive scalp
S-II: Sensitive scalp with severe horny scales
Inflammatory Scalp States (9 Types)
I-I: Scalp on which inflammation began to appear
I-II: Scalp on which inflammation began to appear I-III: Scalp on which inflammation occurred
I-IV: Scalp on which inflammation occurred
I-V: Oily scalp on which inflammation occurred
I-VI: Scalp on which inflammation began to occur (I-I) and horny scales were observed
I-VII: Oily scalp on which inflammation occurred and horny scales were observed
I-VIII: Scalp on which inflammation occurred to cause hair loss
I-IX: Scalp on which seborrheic dermatitis occurred
Oily Scalp States (10 Types)
O-I: Oily scalp
O-II: Oily scalp
O-III: Scalp on which horny scales began to appear
O-IV: Scalp on which hair follicles began to be obstructed
O-V: Scalp on which hair follicles began to be expanded
O-VI: Scalp that was short of moisture
O-VII: Scalp affected by stress
O-VIII: Oily and sensitive scalp on which horny scales were observed
O-IX: Oily scalp on which inflammation began to occur
O-X: Oily scalp on which inflammation began to occur
Bald Scalp States (3 Types)
M-I: Scalp at the initial stage of hair loss
M-II: Scalp undergoing hair loss (thin newborn hairs)
M-III: Scalp on which hair loss occurred As a result of the scalp examination, determinations were made as to what extent of stimulation was applied to the scalps or which states the scalps were changed. The results are shown in Table 4.

TABLE 4

(Unit: □)

| Time (day) | 0 | 10 | 20 | 30 | 40 | 50 | 60 | 70 | 80 | 90 |
|---|---|---|---|---|---|---|---|---|---|---|
| Hair growth stimulant | M-II | M-II | M-II | M-I | M-I | M-I | O-I | O-I | O-I | O-I |
| Placebo | M-I | M-I | M-I | M-I | M-I | M-I | M-I | M-I | M-I | M-I |
| Minoxidil Product | M-II | M-I | O-III | O-VIII | O-VIII | O-VIII | O-VIII | O-VIII | O-IX | O-IX |

The results of Table 4 illustrate that after 30 days following the spreading of the hair growth stimulant, the state (M-II) of the scalp was improved to the initial state (M-I) of hair loss. After 60 days, hair loss was stopped and both hair density and thickness were increased (O-I type). Further, the experimental results revealed that erythema, horny scales and inflammation were not observed, which indicates no side effect.

As for the placebo, there was no difference in scalp state before and after the spreading. Since the scalps did not sensitively respond to the placebo, no side effect was caused.

The minoxidil product showed rapid effects after 10 days following the spreading. However, the scalps sensitively responded to the minoxidil product, involving occurrence of horny scales and erythema. After 70 days, the states of the scalps were worsened (O-IX type) and inflammation was caused. Accordingly, these results lead to the conclusion that care must be taken not to apply the minoxidil product to people who have weak scalp and suffer from an allergic skin disease.

In conclusion, the hair growth stimulant of the present invention showed excellent stimulatory effects on hair restoration without causing any side effect and toxicity in humans and stimulated hair roots to greatly contribute to hair growth. Therefore, it was confirmed that the hair growth stimulant of the present invention was effective in preventing hair loss and grayness.

INDUSTRIAL APPLICABILITY

As apparent from the above description, the hair growth stimulant of the present invention exhibits excellent stimulatory effects on hair restoration without causing any side effect and toxicity in humans and stimulates hair roots to greatly contribute to hair growth. Therefore, the hair growth stimulant of the present invention is effective in preventing hair loss and grayness. In addition, the hair growth stimulant of the present invention is formulated into a cream or ointment preparation, which is highly effective in promoting the restoration of hair, to considerably shorten the time required for the treatment of hair loss, and increases the amount of blood flowing into the scalp to maintain hair in the anagen phase in a healthy state. Furthermore, the hair growth stimulant of the present invention uses vegetable ingredients that exhibit excellent stimulatory effects on hair restoration and hair growth effects to promote the regrowth of hair in the telogen phase. Therefore, the hair growth stimulant of the present invention causes no side effect in humans. Moreover, the hair growth stimulant of the present invention is softly applicable to the scalp, thus offering convenience in use.

The invention claimed is:

1. A hair growth stimulant comprising:
   a mixture of powdered carbonized chestnut (*Castanea* sp.) burrs and a vegetable oil in a weight ratio of 1:1-3, wherein the carbonized chestnut (*Castanea* sp.) burrs comprise Korean native chestnut burrs, and wherein:
   the vegetable oil is a mixture composed of rice bran oil and at least one oil selected from the group consisting of sesame oil, olive oil, perilla oil, palm oil, castor oil, and bean oil, wherein the rice bran oil comprises a condensate of a volatile component of rice bran; and
   the mixture is composed of the rice bran oil and the at least one oil selected from the group in a weight ratio of 1:3-5.

2. The hair growth stimulant according to claim 1, further comprising a concentrate of the rhizome of the plant *Zingiber officinale*, the weight ratio between the powdered carbonized chestnut (*Castanea* sp.) burrs/vegetable oil mixture and the concentrate being 1:0.1-0.5.

3. The hair growth stimulant according to claim 2, wherein the concentrate is obtained by finely dividing the rhizome of the plant *Zingiber officinale* into pieces, extracting the pieces with an extraction solvent in an amount twenty times greater than that of the divided rhizome of the plant *Zingiber officinale* at 40-100° C. for 4-16 hours to obtain an extract, and heating the extract at 40-70° C. and 50-60 kgf/cm$^2$ until the final concentration reaches ten to thirteen times the concentration of the extract.

4. The hair growth stimulant according to claim 3, wherein the extraction solvent is purified water or a 30-60% diluted alcohol.

5. The hair growth stimulant according to claim 1, wherein the carbonized chestnut burrs (*Castanea* sp.) are obtained by selecting suitable chestnut burrs, washing the selected chestnut burrs with water, drying the washed chestnut burrs, introducing the dried chestnut burrs into a sealed container, and completely incinerating the chestnut burrs at 100-300° C. for 1-8 hours.

6. The hair growth stimulant according to claim 1, wherein the carbonized chestnut burrs (*Castanea* sp.) are passed through a sieve of 180-250 mesh to obtain a powder of the carbonized chestnut burrs.

7. The hair growth stimulant according to claim 1, wherein the rice bran oil is obtained by passing rice bran through a carbonization furnace at 75-350° C. to evaporate volatile substances, collecting the volatile substances at a temperature of 100-300° C., cooling the collected substances in a cooling tower at 50-75° C., and purifying the cooled substances.

8. The hair growth stimulant according to claim 1, further comprising at least one adjuvant selected from blood circulation promoters, local stimulants, hair follicle restorers, and anti-inflammatory/antiseptic agents.

9. The hair growth stimulant according to any one of claims 1 and 2-8, wherein the hair growth stimulant is formulated into a preparation for topical application, hair lotion, hair cream, hair gel, hair rinse or essence.

10. The hair growth stimulant according to claim 9, wherein the preparation for topical application is an ointment or cream.

11. A hair growth stimulant comprising:
20 to 40% by weight of a powder of carbonized nuts of Korean native chestnut trees, 30 to 70% by weight of a vegetable oil and 10 to 20% by weight of a concentrate of the rhizome of the plant *Zingiber officinale*, wherein:
the vegetable oil is a mixture composed of rice bran oil and at least one oil selected from the group consisting of sesame oil, olive oil, perilla oil, palm oil, castor oil, and bean oil, wherein the rice bran oil comprises a condensate of a volatile component of rice bran; and
the mixture is composed of the rice bran oil and the at least one oil selected from the group in a weight ratio of 1:3-5.

12. A method for preparing a hair growth stimulant, the method comprising the steps of:
(a) selecting suitable Korean native chestnut (*Castenea* sp.) burrs, washing the selected chestnut burrs with water, drying the washed chestnut burrs, introducing the dried chestnut burrs into a sealed container, completely incinerating the dried chestnut burrs by heating at 100-300° C. for 1-8 hours to obtain carbonized chestnut burrs;
(b) preparing a vegetable oil mixture, wherein the mixture is composed of rice bran oil and at least one additional oil selected from the group consisting of sesame oil, olive oil, perilla oil, palm oil, castor oil, and bean oil, wherein the mixture is composed of the rice bran oil and the at least one additional oil in a weight ratio of 1:3-5 and wherein the rice bran oil comprises a condensate of a volatile component of rice bran; and
(c) mixing the carbonized chestnut burrs with the vegetable oil mixture in a weight ratio of 1:1-3.

13. The method according to claim 12, further comprising the step of finely dividing the rhizome of the plant *Zingiber officinale* into pieces, extracting the rhizome pieces with an extraction solvent in an amount twenty times greater than that of the rhizome pieces at 40-100° C. for 4-16 hours to obtain a ginger extract, and heating the ginger extract at 40-70° C. and 50-60 kgf/cm$^2$ until the final concentration reaches ten to thirteen times the concentration of the ginger extract.

14. The method according to claim 12, wherein the vegetable oil is rice bran oil obtained by passing rice bran through a carbonization furnace at 75-350° C. to evaporate volatile substances, collecting the volatile substances, cooling the collected substances in a cooling tower at 50-75° C., and purifying the cooled substances.

\* \* \* \* \*